United States Patent [19]

Morgan et al.

[11] Patent Number: 4,980,286

[45] Date of Patent: Dec. 25, 1990

[54] IN VIVO INTRODUCTION AND EXPRESSION OF FOREIGN GENETIC MATERIAL IN EPITHELIAL CELLS

[75] Inventors: Jeffrey R. Morgan, Brighton; Richard C. Mulligan, Cambridge, both of Mass.

[73] Assignee: Whitehead Institute for Biomedical Research, Cambridge, Mass.

[21] Appl. No.: 292,885

[22] Filed: Jan. 3, 1989

Related U.S. Application Data

[63] Continuation of Ser. No. 883,590, Jul. 9, 1986, Pat. No. 4,868,116, which is a continuation-in-part of Ser. No. 752,466, Jul. 5, 1985, abandoned.

[51] Int. Cl.$^5$ ............... C12P 21/00; C12N 15/00; C12N 5/00; C12N 7/00
[52] U.S. Cl. ............... 435/172.3; 435/172.1; 435/69.1; 435/70.1; 435/70.3; 435/235; 435/240.1; 435/240.2; 935/59; 935/62; 935/66; 935/70; 935/71
[58] Field of Search ............... 435/68.1, 69.1, 69.4, 435/70.1, 70.3, 172.1, 172.3, 235, 240.2, 252.3; 935/32, 34, 57, 62, 70, 71

[56] References Cited

U.S. PATENT DOCUMENTS 4,769,317 9/1988 Hefton ............................. 435/1

OTHER PUBLICATIONS

Burnett et al (1983), Chemical Abstract CA 99(7):5122a.

*Primary Examiner*—Richard A. Schwartz
*Assistant Examiner*—Anne Brown
*Attorney, Agent, or Firm*—Hamilton, Brook, Smith & Reynolds

[57] ABSTRACT

Epithelial cells expressing foreign genetic material are described. The foreign genetic material can be DNA or RNA which does not occur in epithelial cells; DNA or RNA which occurs in epithelial cells but is not expressed in them at levels which are biologically significant; DNA or RNA which occurs in epithelial and has been modified so that it is expressed in epithelial cells; and any DNA or RNA which can be modified to be expressed in epithelial cells, alone or in any combination thereof. In addition, epithelial cells of the present invention can express genetic material encoding a selectable marker by which cells expressing the foreign genetic material can be expressed.

16 Claims, 4 Drawing Sheets

IN VIVO INTRODUCTION AND EXPRESSION OF FOREIGN GENETIC MATERIAL IN EPITHELIAL CELLS

SPONSORSHIP

The invention disclosed herein was supported by grants from the National Institutes of Health and the Damon Runyon-Walter Winchell Cancer Fund.

RELATED APPLICATION

This application is a continuation of application Ser. No. 06/883,590, filed July 9, 1986, now U.S. Pat. No. 4,868,116, which is a continuation-in-part of U.S. Ser. No. 06/752,466, filed July 5, 1985 now abandoned.

BACKGROUND

Epidermal Cells

The skin is the largest organ in the human body and consists of two components, the epidermis and the dermis. The dermis is a relatively inert structure which consists of collagen and other matrix materials. The epidermis lies above the dermis and is separated from it by a basement membrane.

The epidermis undergoes constant cell renewal and is regenerated approximately every 26 days. The major cellular constituent of the epidermis is the keratinocyte, which provides an environment for nonkeratinocytes (e.g., melanocytes, Langerhans cells, Merkel cells and various immunological cells) which also occur in the epidermis. Keratinocytes are cells which produce keratin, an insoluble fibrous protein, and are able to form a stratified squamous epithelia. Like other cells in the body, keratinocytes contain an entire complement of all genetic material. Only a small percentage of the genes contained in keratinocytes are, however, expressed at levels which are biologically functional; that is, most of the genes in keratinocytes are not expressed at all or are expressed at such low levels that the poplypeptides they encode are produced in undetectable amounts or concentrations which are biologically nonfunctional or insignificant. Like the epidermis, corneal epithelia and conjunctival epithelia are stratified squamous epithelia and the predominant cell in each of these tissues is the keratinocyte. Keratin is to a large degree responsible for the mechanical protective function of the epidermis. In addition, the epidermis acts as a barrier layer which prevents toxic substances and microorganisms from entering the skin and water and electrolytes from being lost.

The epidermis consists of two major layers. Outermost is the stratum corneum, which is a laminated layer of anucleate cornified cells. Next is a succession of viable inner cell layers, referred to as the malpighian layers from which the cornified cells arise. The malpighian layers are the basal cell layer, the stratum spinosum and the stratum granulosum. The basal cell layer, which lies adjacent to the basement membrane, is the germinative layer in which the majority of cell division occurs. The stratum spinosum is a layer of flattened nucleated cells having characteristic keratohyaline granules. The stratum granulosum lies between the stratum spinosum and the stratum corneum and is considered transitional between the nucleated cells of the former and the anucleate cells of the latter.

As the cells divide in the basal layer, they move upward and progress to the other epidermal layers. As they progress, the keratinocytes undergo changes in shape and cytoplasmic structure. These changes result in the viable, metabolically active cells being transformed into the anucleate, cornified cells of the horny layer; these cells consist of keratin filaments surrounded by a cross linked protein envelope. This progressive transformation is referred to as keratinization.

Epidermal cells are considered to occur in proliferative units or columns. The base of each column is a group of basal cells, which are classified as peripheral or central according to whether they lie beneath the periphery or the center of the column. The central basal cell divides; some of the resulting daughters in turn divide and move to peripheral basal positions. The peripheral basal cells then progress up through the successive epidermal layers. They are transformed into keratinized squamous cells, which ultimately flake off and are lost from the body. The central basal cells, however, are stem cells. Descendants of these stem cells will not die throughout the individual's lifetime. These basal cells are immortal and each time they divide, an immortal daughter cell results. The other daughter cells, as mentioned, become differentiating cells and are ultimately shed from the body. The epidermis is one of only a few tissues in the body which undergo constant cell renewal; these include other epithelia, such as the lining of the small intestine, and bone marrow.

It is possible, using methods developed in recent years to attain interspecies genetic recombination. Genes derived from totally different biological classes are able to replicate and be expressed in a selected microorganism. Therefore, it is possible to introduce into a microorganism genes specifying a metabolic or synthetic function (e.g., hormone synthesis, protein synthesis, nitrogen fixation) which is characteristic of other classes of organisms by linking the foreign genes to a particular viral or plasmid replicon.

Since the late 1970s, progress has been made toward the development of general methods for introducing cloned DNA sequences into mammalian cells. At the present time, however, there is a need for an effective method of introducing genetic material into epithelial cells and enable them to express genetic material which they do not usually express.

DISCLOSURE OF THE INVENTION

The invention described herein is based on the introduction into epithelial cells of foreign genetic material or genetic material not normally expressed in biologically significant concentrations in such cells.

Epithelial cells of this invention have incorporated in them foreign genetic material and express the incorporated foreign genetic material. The foreign genetic material can be DNA or RNA which does not occur in epithelial cells; DNA or RNA which occurs in epithelial cells but is not expressed in them at levels which are biologically significant (i.e., levels sufficient to produce the normal physiological effects of the polypeptide it encodes); DNA or RNA which occurs in epithelial cells and has been modified so that it is expressed in epithelial cells; and any DNA or RNA which can be modified to be expressed in epithelial cells, alone or in any combination thereof. In addition, epithelial cells of the present invention can express genetic material encoding a selectable marker by which cells expressing the foreign genetic material can be identified.

In particular, retroviral vectors have been used to incorporate the foreign genetic material and the genetic material encoding the selectable marker into epithelial cells, particularly keratinocytes. It is also possible to introduce foreign genetic material into other epithelial cells, such as cells of the cornea, the conjunctiva, the lining of the gastrointestinal tract, the lining of the vagina, and the trachea and into bone marrow cells. Expression of these genes by the keratinocytes into which they have been incorporated has also been demonstrated. A method of using retroviral vectors which have recombinant genomes to introduce the two types of genetic material into epithelial cells is also a subject of the present invention.

There are many advantages to epithelial cells of the present invention which make them very useful. For example, an epidermis having keratinocytes of the present invention would actually synthesize the polypeptide (e.g., a hormone, enzyme, drug) encoded by the genetic material incorporated into it according to the present invention. The epidermis would thus serve as a continuous delivery system for that polypeptide. In this way, the often-encountered problem of patient compliance with a prescribed regimen would be avoided because the hormone or other polypeptide would be constantly diffused into the bloodstream. In addition, there is no need for extensive (and often expensive) purification of the polypeptide. Before an isolated polypeptide, such as insulin, can be injected into the body, it must be extensively purified and characterized. Using epithelia having keratinocytes modified according to the present invention, however, once the gene has been isolated, it can be introduced into the cells, which will produce the polypeptide hormone as it would normally be produced. (In the case of insulin, for example, as it would normally be produced in the pancreas.)

Another advantage to the use of a graft having keratinocytes of the present invention is that by controlling the size of the graft, the amount of the polypeptide delivered to the body can be controlled. In addition, because it is a skin graft, it can be excised if there is no longer a need for the polypeptide being produced. For example, if delivery of the polypeptide (hormone, enzyme, or drug) is necessary only for a specific period, the engineered graft can be removed when treatment is no longer needed.

Another important advantage of the delivery system possible as a result of this invention is that because it is a continuous delivery system, the fact that polypeptide hormones have very short half lives is not a drawback. For example, the half life of HGH is about 19 minutes and in the case of native insulin (pure insulin) it is about 3-4 minutes.

Because genes can be introduced into keratinocytes using a retroviral vector, they can be "on" (subject to) the retroviral vector control; in such a case, the gene of interest is transcribed from a retroviral promoter. A promoter is a specific nucleotide sequence recognized by RNA polymerase molecules that start RNA synthesis. It is possible to make retroviral vectors having promoter elements (in addition to the promoter incorporated in the recombinant retrovirus) which are responsible for the transcription of the gene. For example, it is possible to make a construct in which there is an additional promoter modulated by an external factor or cue, and in turn to control the level of polypeptide being produced by the keratinocytes by activating that external factor or cue. For example, heat shock proteins are proteins encoded by genes in which the promoter is regulated by temperature. The promoter of the gene which encodes the metal-containing protein metallothionine is responsive to $Cd^{++}$ ions. Incorporation of this promoter or another promoter influenced by external cues also makes it possible to regulate the production of the polypeptide by the engineered keratinocytes.

DETAILED DESCRIPTION OF THE INVENTION

Figure 1:
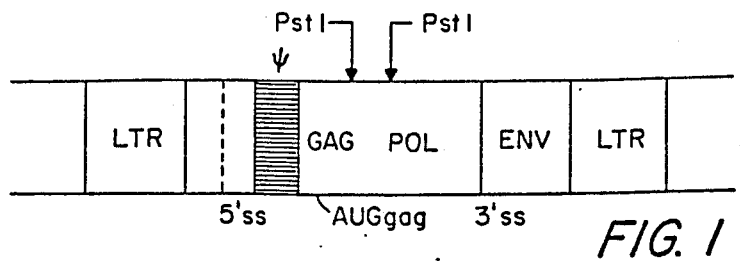
FIG. 1 is a schematic representation of a typical murine leukemia virus (retroviral) genome.

It is possible to incorporate in epithelial cells foreign genetic material which can be expressed in those cells. The foreign genetic material can be DNA or RNA which does not occur in epithelial cells; DNA or RNA which occurs in epithelial cells but is not expressed in them at levels which are biologically significant (levels sufficient to produce the normal physiological effects of the polypeptide it encodes); DNA or RNA which occurs in epithelial cells and has been modified so that it is expressed in epithelial cells; and any DNA or RNA which can be modified to be expressed in epithelial cells, alone or in any combination thereof. Epithelial cells of the present invention express the foreign genetic material. In addition, epithelial cells of the present invention can express genetic material encoding a selectable marker by which cells expressing the foreign genetic material can be identified.

For example, foreign genetic material encoding a hormone can be introduced into keratinocytes by cocultivation of the keratinocytes with a feeder layer producing infectious virus in which there is a recombinant genome having the foreign genetic material. The recombinant genome can also have genetic material encoding a dominant selectable marker. In particular, keratinocytes can be cocultivated with Psi am cells, which produce infectious viruses in which there is a recombinant genome having genetic material encoding human growth hormone. As a result, it is possible to make keratinocytes expressing the neo gene and the foreign genetic material encoding HGH; that is, as a result of this invention, it is possible to make keratinocytes expressing a dominant selectable marker and a polypeptide not normally expressed by such cells at biologically significant levels.

Keratinocytes expressing the two types of genetic material can be grown to confluence; removed as an epithelial sheet from the culture vessel in which they were grown; and applied to the body. Thus applied, the epithelial sheet can provide a continuous supply of the hormone, enzyme or drug made by the keratinocytes. It is possible to modify or regulate the amount of the hormone, enzyme or drug supplied in this way, for example, by using external cues or factors which affect their production; by controlling the size of the epithelial sheet applied; or by removing the epithelial sheet.

Cultured Epidermal Cells

Human keratinocytes can be cultivated in tissue culture under carefully controlled conditions. Green and co-workers have developed techniques which make it possible to grow human epidermal cells or other keratinocytes in cultures with fibroblast cells which have been treated to make them unable to multiply. The presence of fibroblast cell products (supplied from medium harvested from fibroblast cultures) was shown by Green et al. to be essential to support growth of keratinocytes. Fibroblast cell density is controlled in these cultures to allow epidermal cell colony formation and growth. Using the methods developed by Green and co-workers, it is possible to serially culture human epidermal cells and greatly increase the number present in the primary culture. These cocultivation methods are disclosed in U.S. Pat. No. 4,016,036 (1977) ; U.S. Pat. No. 4,304,866 (1981); Green, H. et al., Growth of cultured human epidermal cells into multiple epithelia suitable for grafting, *Proceedings of the National Academy of Sciences, USA*, 76:5665-5668 (1979); Rheinwald, J. G. and H. Green, Epidermal growth factor and the multiplication of cultured human epidermal keratinocytes, *Nature*, 265, 421-424 (1977), the teachings of which are incorporated herein by reference.

Briefly, a specific procedure for the cultivation of keratinocytes involves disaggregation of epidermis into keratinocytes by means of an enzyme (trypsin) and plating of the cells onto a Petri dish on which there is a feeder layer of lethallY irradiated fibroblast cells. The fibroblast cells are able to attach to the dish and provide factors necessary for keratinocyte growth, but are not themselves able to replicate. The cocultivation is carried out in Dulbecco's modified Eagle's media containing 10% fetal calf serum, as well as adenine, cholera toxin, hydrocortisone, transferrin, insulin and epidermal growth factor "Rheinwald and Green" have shown that epidermal growth factor (EGF) affects epidermal keratinocyte colony formation. Rheinwald, J. G. and H. Green, *Nature*, 265:421-424 (1977). A final EGF concentration of 10 ng/ml. was shown to be useful in enhancing cell growth.

Individual keratinocytes cultivated in this way form colonies which expand and grow into larger colonies, which eventually fuse to form an epithelium. This epithelium has several important characteristics which mimic those of the human epidermis. For example, each colony initiated by a single cell forms a stratified epithelium. Cell division occurs in a layer of basal cells (those adjacent to the bottom of the dish). These basal cells are responsible for all cell multiplication and cells that leave the basal layer become terminally differentiated. In addition, there are abundant keratin proteins present in the cultured cells. Epidermal cells cultured in this fashion have the main cytological features of keratinocytes and the cells grown in culture are a reasonable approximation of the epidermis.

Green and co-workers have developed their procedures to the point where it is possible to start with a small epidermal biopsy (about two $cm^2$ in size) and generate large amounts of cultured epithelium in a relatively short time. In about one month, it is possible to produce an epidermis which is approximately two meters square—or enough to cover the entire body surface. These cells have tremendous proliferative capacities in the laboratory and, because they can be cultured so successfully, provide a system of great value. For example, cultured cells have been used as autologous grafts in the treatment of patients with severe burns. O'Connor, N. E., et al., Grafting of burns with cultured epithelium prepared from autologous epidermal cells, *The Lancet*, 75-78 (1981).

Retroviral Vectors

Retroviruses are RNA viruses; that is, the viral genome is RNA. This genomic RNA is, however, reverse transcribed into a DNA intermediate which is integrated very efficiently into the chromosomal DNA of infected cells. This integrated DNA intermediate is referred to as a provirus. As shown in FIG. 1, the retroviral genome and the proviral DNA have three genes: the gag, the pol and the env, which are flanked by two long terminal repeat (LTR) sequences. The gag gene encodes the internal structural (nucleocapsid) proteins; the pol gene encodes the RNA-directed DNA polymerase (reverse transcriptase); and the env gene encodes viral envelope glycoproteins. The 5' and 3' LTRs serve to promote transcription and polyadenylation of virion RNAs.

Adjacent to the 5' LTR are sequences necessary for reverse transcription of the genome (the tRNA primer binding site) and for efficient encapsidation of viral RNA into particles (the $\Psi$, or Psi, site). Mulligan, R. C., Construction of Highly Transmissible Mammalian Cloning Vehicles Derived from Murine Retroviruses, *In: Experimental Manipulation of Gene Expression*, M. Inouye (ed), 155-173 (1983); Mann, R., Mulligan R. C. and Baltimore, D., Construction of a retrovirus packaging mutant and its use to produce helper-free defective retrovirus, *Cell*, 33:153-159 . (1983); Williams, D. A. et al., Introduction of new genetic material into pluripotent haematopoietic stem cells of the mouse, *Nature*, 310:476-480 (1984).

If the sequences necessary for encapsidation (or packaging of retroviral RNA into infectious virions) are missing from the viral genome, the result is a cis defect which prevents encapsidation of genomic RNA. The resulting mutant, however, is still capable of directing the synthesis of all virion proteins. Mulligan and co-workers have described retroviral genomes from which these (Psi) sequences have been deleted, as well as cell lines containing the mutant stably integrated into the chromosome. Mulligan, R. C., Construction of highly transmissible mammalian cloning vehicles derived from murine retroviruses, *In: Experimental Manipulation of Gene Expression*, M. Inouyl (ed), 155-173 (1983); Mann, R., Mulligan R. C. and Baltimore, D., Construction of a retrovirus packaging mutant and its use to produce helper-free defective retrovirus, *Cell*, 33:153-159 (1983); Williams, D. A. et al., Introduction of new genetic material into pluripotent haematopoietic stem cells of the mouse, *Nature*, 310:476-480 (1984). The teachings of these publications are incorporated herein by reference.

As described by Mulligen and co-workers, the Psi 2 cell line was constructed in the following manner: A mutant murine leukemia virus (MuLV) genome in which the region or the genome implicated in the encapsidation of viral RNA into virions is deleted (the Psi sequence in FIG. 2) was constructed. This genome was stably introduced in NIH3T3 cells by DNA cotransformation and stable transformants that produced all of the viral proteins used for encapsidation, yet budded noninfectious particles, were isolated. The mutant of MuLV was constructed by deleting 351 nucleotides from an infectious proviral DNA clone between the putative env mRN4 5' splice site and the AUG that initiates the coding sequence for Pr 65$^{gag}$. The deletion was made from a Bal 1 site to a Pst 1 site and a Hind III site was generated at the point of deletion.

pMOV (pMOVPsi$^-$) was constructed as follows: Three purified DNA fragments were ligated together to construct pMOV Psi$^-$. The first was obtained by digesting pMOV Psi$^+$ with Xho I to completion, followed by partial digestion with Eco RI. Chumakov, I. et al., *Journal of Virology*, 42:1088–1098 (1982). The fragment extending from the Xho I site at 2.0 U in MuLV, through the 3' LTR, 3' mouse flanking sequence, all of pBR322, and ending at the Eco RI site was purified from an agarose gel after electrophoretic separation. Vogelstein, B. and D. Gillespie, *Proceedings of the National Academy of Sciences, USA*, 76I:615–619 (1979). The second fragment was obtained by digestion of pMOV PSI$^+$ with Bal I to completion followed by purification of the fragment extending from the Bal I site in pBR322 through 5' mouse flanking sequence and 5' LTR to the Bal I site located at 0.5 U of MuLV. Hind III linkers (Collaborative Research) were then blunt-ligated to this fragment with T4 DNA ligase, and the fragment was digested with excess Hind III and Eco RI. The LTR-containing fragment was purified from an agarose gel after electrophoretic separation. The third fragment present in the final ligation reaction was obtained from pSV2-gag/pol where the gag/pol region of MuLV had been subcloned into pSV2. Mulligan, R. C. and P. Berg, *Science*, 209:1422–1427 (1980). pSV2-gag/-pol was digested to completion with Xho I and Hind III and the fragment extending from the Hind III site (changed from the Pst I site at 1.0 U of MuLV) to the Xho I site at 2.0 of MuLV was purified from an agarose gel following electrophoretic separation. These three DNA fragments were then mixed in equimolar amounts at a total DNA concentration of 50 μg/ml in ligase buffer (50 mM Tris-HCl [pH 7.8], 10 mM MgCl$_2$, 20 mM dithiothreitol, 1.0 mM ATP, 50 μg/ml bovine serum albumin) and incubated with T4 DNA ligase for 18 hours at 15° C. *E. coli* HB101 was transfected with the ligated DNA, and ampicillin resistant transfectants were obtained. The plasmid DNA obtained from a number of transformants was screened for the desired structure by digestion with appropriate restriction endonucleases and electrophoresis through agarose gels. Davis, R. W. et al., *Methods in Enzymology*, 65:404–411 (1980).

Cell lines containing the Psi$^-$ mutant stably integrated into the chromosome were made by cotransfection of pMOV-Psi$^-$ and pSV2gpt, a SV40 hybrid vector capable of XG PRT expression. Mulligan, R. C. and P. Berg, *Science*, 209:1422–1427 (1980). Cells from gpt$^+$ colonies obtained in this way were cloned and established into three lines: Psi-1, Psi-2 and Psi-3.

The Psi 2 cell line described by Mulligan and co-workers was created by transfecting NIH 3T3 fibroblasts with pMOV-Psi$^-$, which is an ecotropic Moloney murine leukemia virus (Mo-MuLV) clone. pMOV-Psi$^-$ expresses all the Ψ viral gene products but lacks a sequence (the or Psi sequence) necessary for encapsidation of the viral genome. pMOV-Psi$^-$ expresses an ecotropic viral envelope glycoprotein which recognizes a receptor present only on mouse (and closely related rodent) cells.

Another cell line is the NIH Psi am line, which are Psi-2-like packaging cell lines. These Psi-am cell lines contain a modified pMOV-Psi-genome in which the ecotropic envelope glycoprotein has been replaced with envelope sequences derived from the amphotropic virus 4070A. As a result, they are useful for production of recombinant virus with amphotropic host range. The retrovirus used to make the Psi am cell line has a very broad mammalian host range (an amphotropic host range) and can be used to infect human cells. As long as the recombinant genome has the Psi packaging sequence, the Psi-am cell line is capable of packaging recombinant retroviral genomes into infectious retroviral particles.

Figure 2:
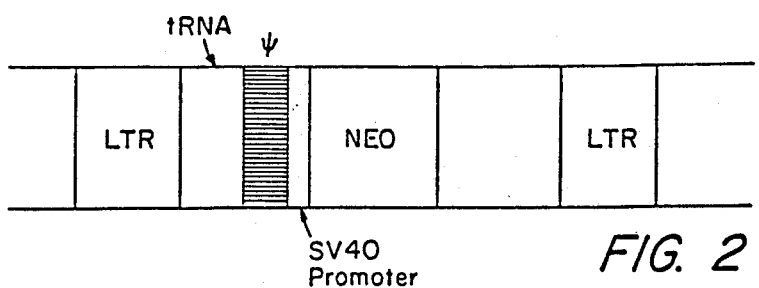
FIG. 2 is a schematic representation of a recombinant retroviral genome into which the neo gene has been incorporated.

The retroviral genome has been modified by Cone and Mulligan for use as a vector capable of introducing new genes into cells. As shown in FIG. 2, the gag, the pol and the env genes have all been removed and a DNA segment encoding the neo gene has been inserted in their place. The neo gene serves as a dominant selectable marker. The retroviral sequence which remains part of the recombinant genome includes the LTRs, the tRNA binding site and the Psi packaging site. Cone, R. and Mulligan, R., High-efficiency gene transfer into mammalian cells: Generation of helper-free recombinant retrovirus with broad mammalian host range, *Proceedings of the National Academy of Sciences, U.S.A.*, 81:6349–6353 (1984).

I. Introduction of a Dominant Selectable Marker into Keratinocytes and Verification of its Insertion A. Introduction of the neo gene into Keratinocytes A cell line producing recombinant amphotropic retrovirus having a recombinant genome is used in cocultivation with keratinocytes. As shown in FIG. 2, the recombinant genome is comprised of two LTRs and, in place of the gag, the pol and the env sequences, a neo gene. The Psi am cell line, originally derived from a 3T3 cell line which can be modified using standard techniques to include the recombinant retroviral genome, has been deposited with the American Type Culture Collection (Rockville, Md.) under deposit number CRL8859.

The neo gene is a bacterial gene derived from the transposon Tn5, which encodes neomycin resistance in bacteria and resistance to the antibiotic G418 in mammalian cells. This neo gene acts as a dominant selectable marker; its presence in a mammalian cell converts the cell into one which will grow in the presence of G418. (In its absence, the cell dies in the presence of G418.) As a result, the presence of this gene in a mammalian cell can be determined by selection for its presence in cells grown in media which contains G418. The recombinant retrovirus having this recombinant genome is referred to as the neo virus.

In one embodiment of this invention, the fibroblast cell line used as the feeder layer for (in cocultivation with) keratinocytes is a Psi am line producing the neo virus at relatively high titers (e.g., between $10^4$ and $10^5$ neo units per mil). The neo gene is introduced into keratinocytes by means of this retroviral vector and its presence in the keratinocytes verified.

Figure 3:
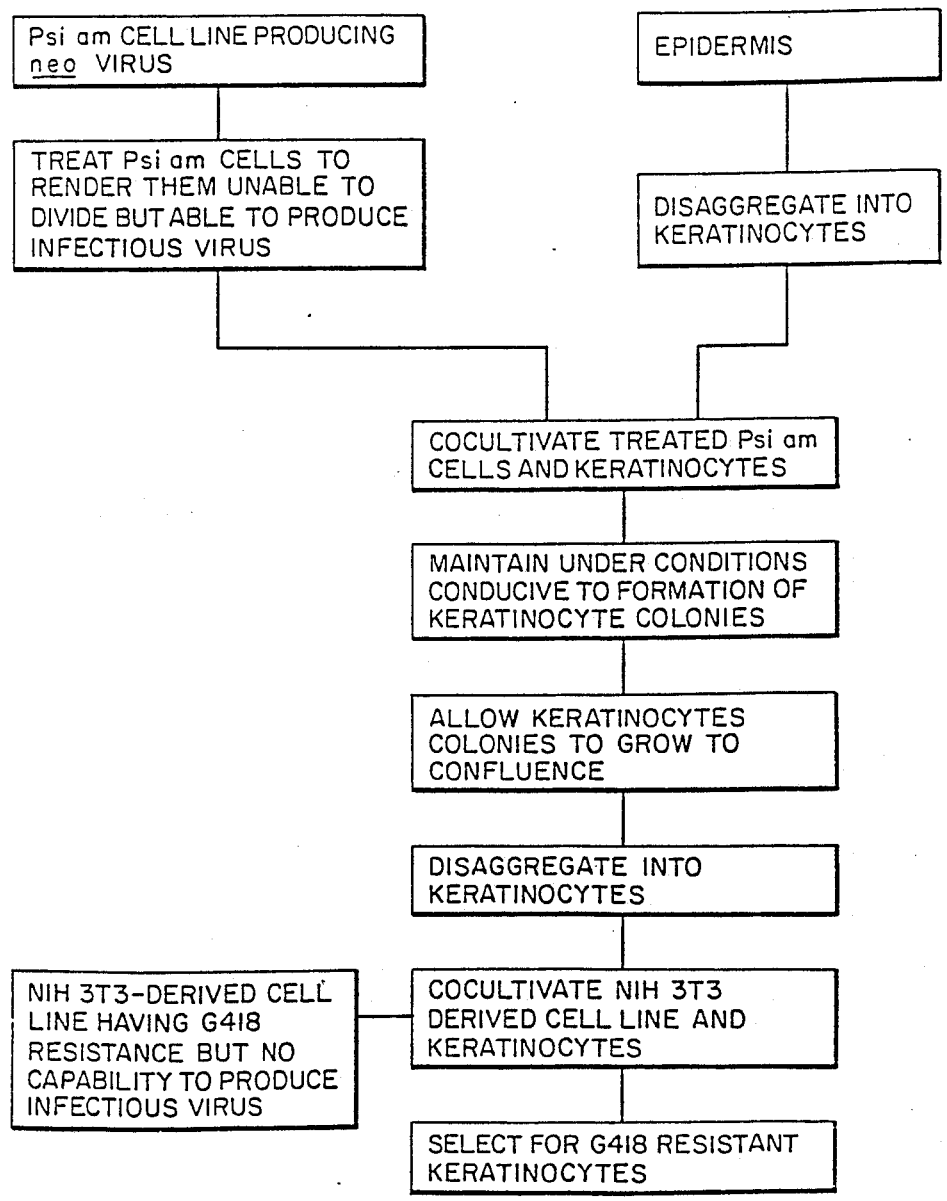
FIG. 3 is a block diagram of one embodiment of the method used to introduce a dominant selectable marker (the neo gene) into keratinocytes.

In this embodiment the neo gene was introduced into keratinocytes according to the procedure represented in FIG. 3. The procedure is described in detail in Example 1. Psi am line producing the neo virus was treated with mitomycin C, which is an antibiotic which crosslinks DNA and thus renders the cells unable to divide. They are, however, still capable of producing infectious virus. The suspension of keratinocytes was plated onto a dish containing the treated Psi am cells, which served as a feeder layer producing infectious virus.

Keratinocyte colonies formed and grew to confluence. At that point, the cells were disaggregated and plated onto a different feeder layer which had also been treated with mitomycin C. Like the Psi am line, this feeder layer is resistant to G418 (because it has been engineered to contain the neo gene). Unlike the Psi am line, it goes not produce infectious virus. As a result, it can serve as a feeder layer during the selection process. This is referred to as the G418 feeder layer.

The disaggregated keratinocytes were plated on this G418 resistant feeder layer and G418 was added to the culture. After incubation, those cells which were growing up were resistant to G418; there were no colonies growing up from control cells (uninfected cells). The G418 resistant cells appeared to be viable normal keratinocyte colonies, indicating that the neo gene had been introduced into and expressed in these cells via the retroviral vector.

B. Verification of the Introduction of the neo gene into Keratinocytes and of the Characteristics of Keratinocytes Having the neo gene It is possible, through the use of the recombinant retrovirus (the neo virus) to introduce new genetic material into keratinocytes without altering the functional characteristics of the recipient keratinocytes. That the neo gene had been introduced into keratinocytes and that the recipient cells were in fact viable keratinocytes has been verified. The procedures used are described in greater detail in Example 2.

To demonstrate that these G418 resistant keratinocytes contain the neo gene, analyses were performed on DNA extracted from G418-resistance keratinocytes and fragmented. On the basis of differences in the molecular weights of the DNA extracted from feeder cells and the DNA extracted from keratinocytes, it was possible to detect the neo gene in the keratinocytes; a neo gene was not evident in the uninfected cells. The neo gene in the keratinocytes was different in size from the neo gene present in the feeder layer.

It has also been shown that the keratinocytes containing the neo gene are of the normal wild type. This has been demonstrated in several ways. For example, total cell protein extracted from infected and uninfected cells; was fractionated electrophoretically and visualized. The protein profile of the infected cells was very distinctive of keratinocytes. There are four major keratin proteins in keratinocytes (58, 56, 50 and 46 Kd in size) and these were at normal levels, both qualitatively and quantitatively, in the uninfected and the infected keratinocytes. Analysis by Western blotting demonstrated the presence of involucrin. Involucrin is the precursor protein of the crosslinked envelope which is distinctive of terminal differentiation in keratinocytes and is therefore a distinctive terminal differentiation marker of keratinocytes. The G418 resistant keratinocytes were also shown by electron microscopy to have the appearance of normal keratinocytes: that is, G418 resistant keratinocytes colonies were five or six cell layers thick and contained keratin filaments, tonofilaments, and numerous desmosomes—all hallmarks of normal keratinocyte colonies.

G418-resistant keratinocytes have also been grown to confluence, segregated as an intact epithelium and transplanted onto athymic or nude mice. This approach demonstrates the ability of the epidermis to continue to differentiate, a process only partially evident in tissue culture. This is carried out in the following manner which is described in greater detail in Example 3. G418 resistant keratinocytes were grown using the G418 feeder layer; growth continued until adjoining colonies fused and became confluent. The sheet of epidermal cells was lifted off the dish, at which point, it contracted to about half the size of the culture vessel. The epithelium was transplanted to an appropriate recipient, which in this case was an athymic or nude mouse. Because the athymic or nude mouse lacks a thymus, it is incapable of rejecting transplanted tissue.

To determine whether the transplant worked, thin sections of this epidermis were made about two weeks after transplantation and the presence of involucrin determined. This was done for example, by immunoassay making use of antibodies to involucrin, which, as mentioned previously, is a distinctive terminal differentiation marker for keratinocytes. As a result, it has been demonstrated that new genetic material was introduced into the keratinocytes by means of the retroviral vectors described above. In addition, it has been shown that this information could be expressed by the keratinocytes; that is, selection for keratinocytes resistant to G418 indicated expression of the neo gene.

II. Introduction of a Dominant Selectable Marker and Foreign Genetic Material into Keratinocytes and Assessment of Expression of the Foreign Genetic Material The recombinant retroviral vectors having the neo gene also have a cloning site. This makes it possible to introduce foreign genetic material into the vector and to have it expressed by keratinocytes cocultivated with the recombinant retrovirus. At the Bam Hl cloning site, it is possible to insert foreign genetic material. The foreign genetic material can be DNA or RNA which does not occur in epithelial cells; DNA or RNA which occurs in epithelial cells but is not expressed by them at levels which are biologically effective (i.e., levels sufficient to produce the normal physiological effects of the polypeptide it encodes); DNA or RNA which occurs in epithelial cells and has been modified so that it is expressed by epithelial cells; and any DNA or RNA which can be modified to be expressed by epithelial cells, alone or in any combination thereof. For example, it is possible to clone into this site in the retroviral vector a copy of the gene encoding human growth hormone (HGH). HGH is a polypeptide of about 29,000 Daltons which is normally secreted only by the hypothalamus. Although the HGH gene is present in keratinocytes, it is not expressed in those cells at biologically significant levels. Keratinocytes capable of making a polypeptide hormone such as HGH, or another substance not normally made by such cells at biologically significant levels, can be transplanted onto an individual and serve as a continuous supply system for the hormone or other substance.

Figure 4:
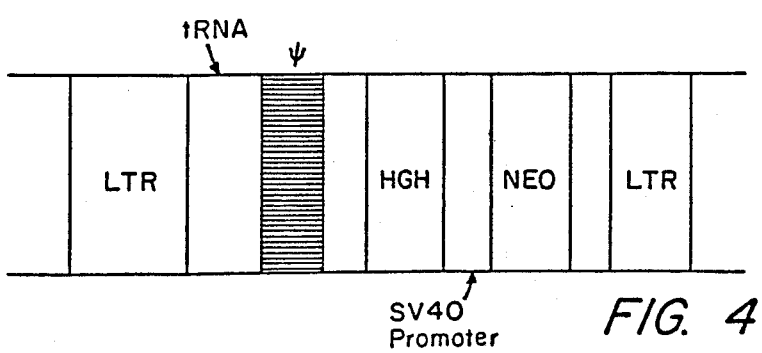
FIG. 4 is a schematic representation of a recombinant retroviral genome having the neo gene and a gene encoding human growth hormone (HGH).

This process is described with reference to human growth hormone, but it is to be understood that any gene could be introduced into keratinocytes and its expression by the cells assessed in a similar manner. The procedure is described in greater detail in Example 3. A Psi am line which produces a recombinant retrovirus having the gene of interest—here, the human growth hormone gene—can be constructed. A modified DNA segment encoding a cDNA of human growth hormone is ligated into the Bam Hl site of plasmid DNA having a recombinant retroviral genome; in one embodiment, this is the neo gene. The plasmid is isolated and transfected onto Psi am cell. Psi am cells producing the HGH-neo recombinant virus construct, which is represented in FIG. 4, are isolated as G418 resistant colonies.

The Psi am cells producing the HGH-neo recombinant virus construct are used as the feeder layer in cocultivation with disaggregated keratinocytes. After cocultivation with the Psi am cells producing the HGH-neo recombinant virus construct, the keratinocytes are allowed to grow to confluence; are disaggregated into keratinocytes; and cocultivated with the G418 resistant cell line as previously described.

The ability of keratinocytes, which have been cocultivated with the recombinant retrovirus having a recombinant genome containing foreign genetic material, to express the foreign genetic material can be assessed using several techniques. These techniques are described in greater detail in Example 3.

As a result, it has been demonstrated that keratinocytes are able to secrete a polypeptide hormone which is normally not secreted at biologically significant levels by keratinocytes and, additionally, that they can secrete this hormone at close to physiological concentrations. Transplantation of the epithelium which is secreting human growth hormone (e.g., onto an athymic mouse) can be used to demonstrate whether it can secrete sufficient quantities to produce a systemic effect. The manner in which this transplantation of epidermis having keratinocytes in which new genetic material (e.g., the neo gene and a selected gene encoding a polypeptide of interest) can be done is outlined in FIG. 5.

Figure 5:
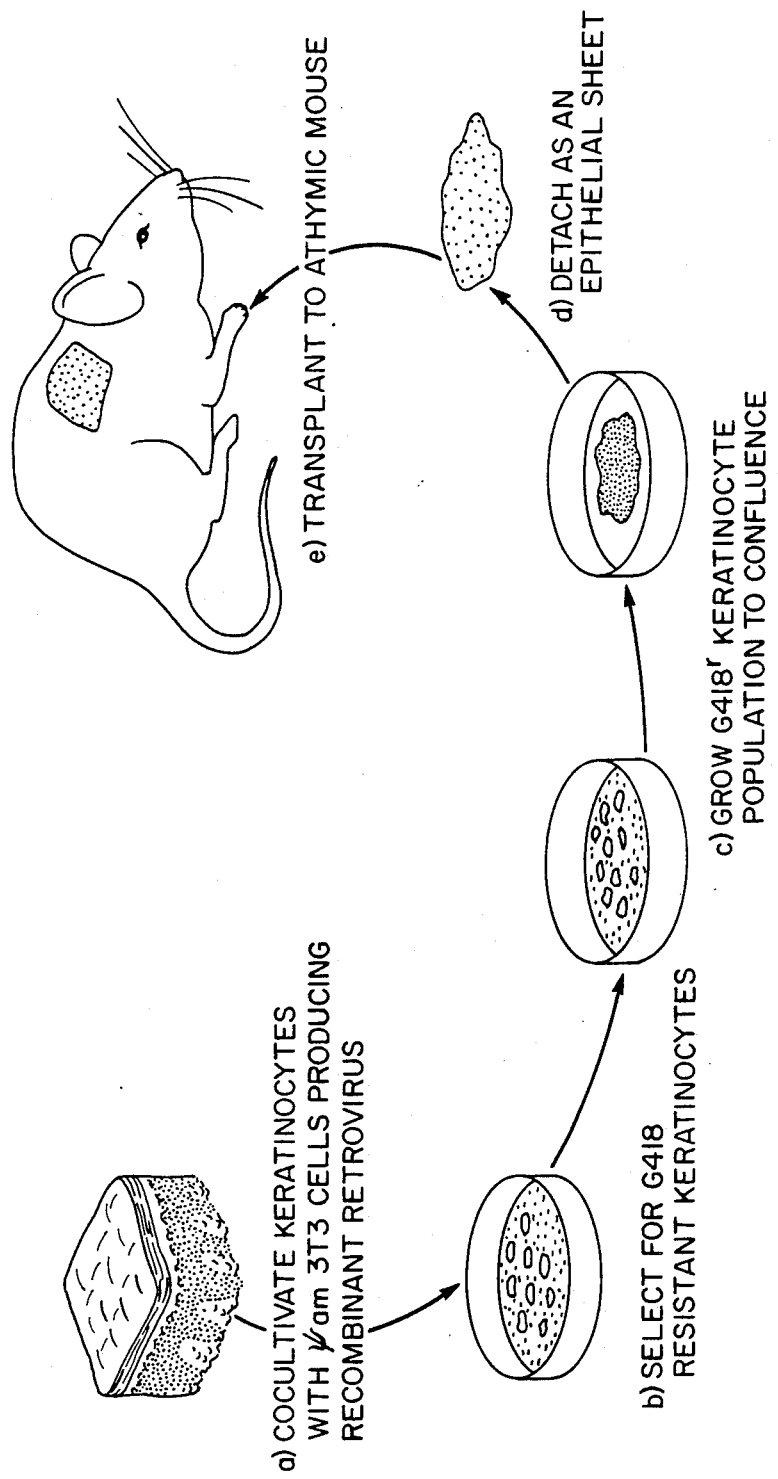
FIG. 5 is a pictorial representation of one embodiment of the procedure used to produce, detach and transplant an epithelial sheet in which the keratinocytes have foreign genetic material and genetic material encoding a dominant selectable marker.

It is possible to make an epithelium, in which the keratinocytes have new genetic material, suitable for grafting onto a recipient. The recipient could be the original source of the epithelial cells or could receive a graft from an appropriately matched donor. As shown in FIG. 5, a section of epidermis is disaggregated into individual keratinocytes, which are cocultivated with a Psi am line producing both the neo gene and the gene of interest. G418-resistant keratinocytes are selected, grown to confluence and detached as an epithelium. The detached epithelium is subsequently grafted onto the recipient.

At the present time, children who are dwarves because of a genetic lesion are treated with human growth hormone administered daily by injection. These patients could be treated by a skin graft having keratinocytes secreting human growth hormone.

III. Introduction of the neo gene and Foreign Genetic Material Encoding Polypeptides Other Than HGH Genes encoding polypeptides other than HGH can also be introduced into keratinocytes by means of the retroviral vector. For example, genes encoding parathyroid hormone (PTH) and insulin have been introduced into keratinocytes along with the neo gene. Parathyroid hormone is a polypeptide involved in the regulation of calcium in the body. Insulin is a polypeptide which regulates glucose levels in the bloodstream. Unlike HGH, each of these polypeptide hormones requires processing of the polypeptide before it can be active. For example, parathyroid hormone has a presequence and a presequence at the amino terminus of the protein. Insulin is a peptide made of a and b chains which are connected by disulfide bonds. The precursor to insulin, however, contains another peptide, the c peptide. During the processing this c peptide must be cleaved out in order to yield active insulin molecules. To date, this cleavage has been shown to be carried out in pancreatic cells and possibly by neuron cells.

IV. Use of Other Dominant Selectable Markers in the Introduction of Genetic Material Encoding Polypeptides It is also possible tO use dominant selectable markers other than the neo gene to introduce new genetic material into keratinocytes. For example, the His D gene can be used for this purpose. The His D gene is a bacterial gene from Salmonella and encodes histidinol dehydrogenase, a polypeptide which converts histidinol to histidine. Histidine is an essential amino acid; histidinol is an alcohol analogue of histidine and can be converted to histidine under the proper metabolic conditions. If cells are grown in media containing histidinol but lacking histidine, those cells having the His D gene can convert histidinol to histidine. Because histidine is essential to their function, those cells which have the His D gene (and thus can make histidine) will survive and those lacking the gene will not.

A retrovirus vector having the His D gene has been used to infect keratinocytes. The keratinocytes containing His D gene were selected by growing these cells in media lacking histidine but containing histidinol. As expected, keratinocytes having the His D gene formed colonies and grew to confluence; those lacking the gene did not. In fact, such cells occurred at a much higher frequency than those in which the neo gene was included.

As a result of this work, it is also possible to use independent dominant selectable markers (e.g., the neo gene and the His D gene) to introduce new genetic material into keratinocytes. In the case of polypeptides which have two different subunits, for example, separate dominant selectable markers could be used to introduce the genetic information encoding the two subunits. In addition, two or more dominant selectable markers could be used in the case of polypeptides which need to be specifically cleaved or processed in order to become active (e.g., insulin and parathyroid hormone). A gene encoding the necessary processing enzyme could be introduced along with the gene encoding the polypeptide hormone requiring such processing. This would enable keratinocytes to process that polypeptide hormone.

V. Uses of Keratinocytes Having Foreign Genetic Material

It is also possible to use vehicles other than retroviruses to genetically engineer or modify keratinocytes and other epithelial cells. New genetic information could be introduced into keratinocytes by means of any virus which can express the new genetic material in such cells. For example, SV40, Herpes virus, Adeno virus and human papilloma virus could be used for this purpose. Human papilloma virus, which causes warts, may be particularly useful for at least three reasons. First, this virus naturally infects keratinocytes. Second, its genome is circular and in transformed cells, it remains circular and replicates extrachromosomally (e.g., its DNA does not integrate into genomic DNA of transformed cells, as retroviral DNA does). Third, a large number of copies (e.g., between 50 and 200) of the viral DNA is made per transformed cell. This is particularly useful because transformed cells are therefore able to produce large quantities of the polypeptide encoded by the new genetic material (e.g., hormone, enzyme, etc.).

The present invention makes it possible to genetically engineer keratinocytes capable of forming epithelia which can secrete products (e.g., clotting factors, immunoregulatable factors, and polypeptide hormones) into the bloodstream. The epithelia formed in this way can serve as a continuous drug delivery system to replace present regimens, which require periodic administration (by ingestion, injection, etc.) of the needed substance. For example, it could be used to provide continuous delivery of insulin, which at the present time, must be isolated from the pancreas, extensively purified and then injected into the body by those whose insulin production or utilization is impaired. In this way, insulin could be introduced into the body via a continuous drug delivery system and there would be no need for daily injections of insulin. Genetically engineered epidermis can also be used for the production of clotting factors. Hemaphiliacs lack a protein called Factor VIII, which is involved in clotting. Factor VIII is now administered by injection; keratinocytes having genes encoding Factor VIII, can be used to make epithelia and producing Factor VIII; as a skin graft, the tissue would secrete the factor into the bloodstream.

Another application for an epidermis having genetically engineered keratinocytes is in birth control. Tests are underway now for using a polypeptide hormone called lutenizing hormone releasing hormone (LHRH) in regulating fertility. Continuous administration of LHRH results in a sterile individual; when administration ceases, the individual is again fertile. Rather than taking LHRH injections or oral medication, one could have a small graft continuously secreting LHRH to provide the same effect. In the event that the person wanted to regain fertility this transplant could be excised and delivery of the polypeptide hormone would cease.

Another application of keratinocytes having new genetic material is in the treatment of Acquired Immune Deficiency Syndrome (AIDS). Interleukin 2 and Interleukin 3, which stimulate the immune system, are potentially valuable in the treatment of AIDS and could be delivered by a skin graft having keratinocytes genetically engineered to produce these two polypeptides (which are now administered by periodic injection).

Another use of genetically engineered keratinocytes is to change hair growth patterns in an individual or to grow hair in culture for transplantation. Because hair formation is genetically controlled and hair is an epidermal appendage, keratinocytes have potential use in changing hair growth.

Another application is to improve the general properties of the skin. The skin has several important properties. It provides a barrier to the external surface, is a highly elastic structure, is resilient and has very excellent protective qualities. The recombinant retroviral vector of this invention could be used to introduce genes into the skin which would improve its consistency or improve the basic function of the skin. As an example, the epidermis which is found on the soles of the feet and the heels and palms of the hands is much thicker than the epidermis found in other areas of the body. In addition, that epidermis contains a keratin protein of a distinct molecular weight. Once this gene is cloned, it can be introduced into a skin transplant that could be placed in an area where a tougher skin is desirable. For example, this might be useful in the case of an immobilized patient, for whom bed sores might be a severe problem. A skin graft could be engineered to be much tougher and more resilient than skin occurring in those areas where bed sores develop (e.g., back buttocks, legs); its application could provide protection for that patient. Another potential use which requires changing the skin's characteristics is in treatment of victims with severe burn. In this case there are several needs for skin to grow very rapidly in order to prevent infection, etc. Using this vector system, it is possible to engineer a skin or an epidermis which would be much more suitable for someone who had a severe burn.

Another use of the present invention is in the treatment of enzyme defect diseases. In this case the product (polypeptide) encoded by the gene introduced into keratinocytes is not secreted (as are hormones), but is an enzyme which remains inside the cell. There are numerous cases of genetic diseases in which the patient lacks a particular enzyme and is not able to metabolize various amino acids or other metabolites. The correct genes for these enzymes could be introduced into a skin transplant; the transplant would then carry out that metabolic function. For example, there is a genetic disease in which those affected lack the enzyme adenosine deaminase. This enzyme is involved in the degradation of purines to uric acid. It might be possible, using the present invention, to produce a skin graft capable of producing the missing enzyme at sufficiently high levels to detoxify the blood as it passes through the area to which the graft is applied.

Epithelial cells having foreign genetic material introduced according to the present invention can also be used as transdermal drug delivery systems. In such systems, the drug is applied to the surface of the epidermis and diffuses into the bloodstream through the epidermis. An example of transdermally administered drugs are currently used for prevention of motion sickness. An important limitation to transdermal drug delivery, however, is that the drug must be permeable to the epidermal outer layers; it must be lipid soluble in order to be able to penetrate these layers and be effective.

This limitation can be eliminated, however, using epidermis having keratinocytes modified according to the present invention. For example, in the case of a drug which (in its active form) is not lipid soluble, the drug could be made in a lipd soluble—but inactive—form which can pass through the epidermis. It can then be applied to a skin graft having keratinocytes genetically engineered to be able to convert the lipid soluble/inactive drug into a water soluble/active form. The drug could then pass into the bloodstream and produce the desired effect.

The present invention also has veterinary applications. It can be used, for example, in delivering substances such as drugs (e.g., antibiotics) and hormones to animals, which would otherwise be provided by being incorporated into their feed, added to their water or injected periodically (e.g., daily or less frequently). Use of the modified epithelial cells of the present invention has the advantage that the tissue formed of the modified epithelial cells can be applied to the animal and will provide quanitites of the encoded protein on an ongoing basis, thus eliminating the need for daily/periodic administration of the substance.

This invention will now be illustrated by the following examples.

EXAMPLE 1 INTRODUCTION OF A NEO GENE INTO KERATINOCYTES

The neo gene was introduced into keratinocytes according to the procedure represented in FIG. 3. Psi am line producing the neo virus was treated with mitomycin C at 5 micrograms per mil at about 37° for about two hours in Dulbecco's Modified Eagle's Media (DME) without serum. Mitomycin C is an antibiotic which crosslinks DNA and thus renders the cells unable to divide. However, the cells are still capable of producing infectious virus. Psi am cells were treated with mitomycin C on a 10 centimeter dish and washed several times with DME. The suspension of keratinocytes was plated onto this dish. As a result, the feeder layer used was one producing infectious virus.

Keratinocyte colonies formed several days later and grew to confluence. At that point the cells were trypsinized (treated with the enzyme trypsin) to disaggregate them into single cells and plated onto a different feeder layer which had also been treated with mitomycin C. Like the Psi am line, this feeder layer is G418 resistant (because it has been engineered to contain the neo gene). Unlike the Psi am line, it does not produce infectious virus. As a result, it can serve as a feeder layer during the selection process. This is referred to as the G418 feeder layer.

The disaggregated keratinocytes were plated on this G418 resistant feeder layer and G418 was added at a final concentration in the media of between 0.5 and 1 mgs. per mil. After about two weeks or incubation, those cells which were growing up were resistant to G418; there were no colonies growing up from control cells (uninfected cells). The G418 resistant cells appeared to be viable normal keratinocyte colonies, indicating that the neo gene had been introduced into and expressed in these cells via the retroviral vector.

EXAMPLE 2 VERIFICATION OF THE INTRODUCTION OF THE NEO GENE INTO KERATINOCYTES AND CHARACTERIZATION OF KERATINOCYTES HAVING THE NEO GENE

It is possible, through the use of the recombinant retrovirus (the neo virus) to introduce new genetic material into keratinocytes without altering the functional characteristics of the recipient keratinocytes. That the neo gene had been introduced into keratinocytes and that the recipient cells were in fact viable keratinocytes has been verified.

To demonstrate that these G418 resistant keratinocytes contain the neo gene, a Southern blot analysis was performed on DNA extracted from G418-resistance keratinocytes. Maniatis, T. et al., *In: Molecular Cloning: A Laboratory Manual*, Cold Spring Harbor, N.Y. (1982). The DNA was digested by restriction enzymes and a Southern blot hybridization analysis performed. On the basis of differences in the molecular weights of the DNA extracted from feeder cells and the DNA extracted from keratinocytes, it was possible to detect the neo gene in the keratinocytes; a neo gene was not evident in the uninfected cells. The neo gene in the keratinocytes was different in size from the neo gene present in the feeder layer.

It has also been shown that the keratinocytes containing the neo gene are of the normal wild type. This has been demonstrated in several ways. For example, total cell protein was extracted from infected and uninfected cells; fractionated by SDS polyacrylamide elecrophoresis; and visualized by staining by Coomasie blue stain. The protein profile of the infected cells was very distinctive of keratinocytes. There are four major keratin proteins in keratinocytes (58, 56, 50 and 46 Kd in size) and these were at normal levels, both qualitatively and quantitatively, in the uninfected and the infected keratinocytes.

The presence of involucrin was also determined. Involucrin is the precursor protein of the crosslinked envelope which is distinctive of terminal differentiation in keratinocytes. It is therefore a distinctive terminal differentiation marker of keratinocytes. A Western blotting technique demonstrated the presence of involucrin. Towbin, H. et al., *Proceedings of the National Academy of Sciences, U.S.A.*, 76:4350–4354 (1979). The G418 resistant keratinocytes were also shown by electron microscopy to have the appearance of normal keratinocytes. The EM pictures show that the G418 resistant keratinocytes colony was five or six cell layers thick. They also reveal the presence of keratin filaments, tonofilaments, and numerous desmosomes—all hallmarks of normal keratinocyte colonies.

The G418-resistant keratinocytes have also been grown to confluence, segregated as an intact epithelium and transplanted onto athymic or nude mice. This approach demonstrates the ability of the epidermis to continue to differentiate, a process only partially evident in tissue culture. This was carried out in the following manner. The G418 resistant keratinocytes were grown on a Petri dish, using the G418 feeder layer, until adjoining colonies fused and the dish was covered with keratinocytes. Using an enzyme called Dispase, the sheet of epidermal cells was lifted off the dish using the method described by Green and Kehinde. Green, H. and Kehinde, O., U.S. Pat. No. 4,304,866; Green, H. et al., Growth of cultured epidermal cells into multiple epithelia suitable for grafting, Proceedings of the National Academy of Sciences, U.S.A., 76:5665–5668 (1979). At that point, the sheet contracted to about half the size of the dish. The epithelium was placed on Vaseline gauze and transplanted to an athymic or nude mouse. Because the athymic or nude mouse lacks a thymus, it is incapable of rejecting transplanted tissue.

To determine whether the transplant has worked, thin sections of this epidermis are made about two weeks after it is transplanted. Using antibodies to involucrin, which is a protein distinctive of human epidermis and, as mentioned previously, a distinctive terminal differentiation marker for keratinocytes, the presence of transplanted human epidermis was detected. As a result, it has been demonstrated that new genetic material was introduced into the keratinocytes by means of the retroviral vectors described above. In addition, it has been shown that this information could be expressed by the keratinocytes; that is, selection for keratinocytes resistant to G418 indicated expression of the neo gene.

EXAMPLE 3 INTRODUCTION OF THE NEO GENE AND FOREIGN GENETIC MATERIAL INTO KERATINOCYTES

A. Introduction of the neo gene and the gene encoding human growth hormone (HGH)

The recombinant retroviral vectors having the neo gene also have a cloning site. This makes it possible to introduce foreign genetic material into the vector and to have it expressed by keratinocytes cocultivated with the recombinant virus. It is possible to insert the foreign genetic material at the Bam Hl cloning site. For example, it is possible to clone into this site in the retroviral vector a copy of the gene encoding human growth hormone (HGH). HGH is a polypeptide of about 29,000 Daltons which is normally secreted only by the hypothalamus. Keratinocytes capable of making a polypeptide hormone (such as HGH) or another substance not normally made by such cells could be transplanted onto an individual and serve as a continuous supply system for the hormone or other substance.

This process is described with reference to human growth hormone, but it is to be understood that any gene could be introduced into keratinocytes and its expression by the cells assessed in a similar manner. A Psi am line which produces a recombinant retrovirus having the gene of interest —here, the human growth hormone gene—was constructed in the following way. Plasmid DNA having the recombinant retroviral genome (having the neo gene) was digested with Bam Hl. A modified DNA segment encoding a cDNA of human growth hormone was ligated into this site. The plasmid having the proper orientation of the HGH gene was isolated and transfected onto Psi am cell using the $Ca^{++}$ phosphate technique. Graham, R. and Vander Eb, A., *Virology,* 52:456–467 (1973). Psi am cells producing the HGH-neo recombinant virus construct, which is represented in FIG. 4, were isolated as G418 resistant colonies.

The Psi am cells producing the HGH-neo recombinant virus construct were used as the feeder layer in cocultivation with disaggregated keratinocytes. The same procedure as described previously for introduction of the neo gene alone was followed to introduce the HGH-neo construct into keratinocytes. That is, after cocultivation with the Psi am cells producing the HGH-neo recombinant virus construct, the keratinocytes were allowed to grow to confluence; were disaggregated into keratinocytes; and cocultivated with the NIH 3T3 derived cell line having G418 resistance as previously described.

B. Assessment of Expression of the Human Growth Hormone Gene by the Keratinocytes The keratinocytes were assessed for their ability to express the foreign genetic material (in this case, the human growth hormone gene).

An immunoprecipitation method utilizing keratinocytes metabolically labeled with 35 S methionine was used to detect the presence of HGH in the cultured keratinocytes. In the case of human growth hormone, which is secreted into the media, supernatants were assayed. Antibody specific to HGH was added to the media and allowed to complex with the HGH. The antibody-HGH complex was precipitated using Staphylococus aureus bacteria bugs known to precipitate them. The complex was treated (e.g by washing and boiling in an SDS buffer) so as to separate the two components. After being fractionated on an SDS polyacrylamide gel and dried down, the radioactive proteins were visualized by autoradiography. With specific size markers it was possible to detect the presence of HGH secreted into the media. That is, using protein standards having known molecular weights, it is possible to construct a standard curve showing molecular weight against distance travelled on the gel and to determine the molecular weight of the protein secreted by the keratinocytes. A highly purified $^{125}I$ labelled HGH was used as a very specific marker. Therefore the results are highly conclusive in the identification of HGH. Secretion of HGH was shown to be unique to the keratinocytes with the HGH-neo recombinant virus; uninfected keratinocytes and those infected solely with the neo virus secreted no HGH. Keratinocytes having the HGH-neo recombinant virus are on deposit with the American Type Culture Collection (Rockville, Md.) under deposit number CRL8858.

Using radioimmuno assay, which is an excellent method for determining precise amounts of the hormone, it was possible to determine that there was in excess of 30 to 50 nanograms HGH per milliter in the media. This shows that HGH is secreted by the keratinocytes at levels which are similar to physiological concentrations. (Human serum normally contains 1-5 ng HGH per mil.)

Thus, this demonstrates that keratinocytes are able to secret a polypeptide hormone which is normally not secreted by keratinocytes and, additionally, that they can secrete this hormone at close to physiological concentrations.

EXAMPLE 4 INTRODUCTION OF FOREIGN GENETIC MATERIAL AND DETERMINATION OF GRAFT SIZE NEEDED FOR PRODUCTION OF ENCODED MATERIAL AT PHYSIOLOGICALLY SIGNIFICANT LEVELS

A. Introduction of the neo gene and the gene encoding parathyroid hormone (PTH)

A recombinant retrovirus containing a copy of the gene encoding parathyroid hormone (PTH) was constructed according to the method described in Example 3. The resulting construct was introduced into human keratinocytes by the method described in Example 3. Keratinocytes resistant to G418 were selected and the population of such cells expanded and allowed to grow to confluence.

Confluent cultures of G418 resistant keratinocytes were assayed for synthesis and secretion of PTH in the following manner. A 75 $cm^2$ flask of a confluent culture of modified keratinocytes was used for measurement of the quantity of PTH secreted. At time zero, the media was removed and 20 m.l. of fresh media added. At 4 hour intervals, aliquots of the media were removed and frozen. The level of PTH in these aliquots was measured using a standard radioimmune assay specific for PTH. The result of the assays are as follows:

| Time (hours) | PTH/20 ml. (micrograms) |
|---|---|
| 4 | 2.2 |
| 8 | 4.0 |
| 12 | 6.0 |
| 16 | 7.0 |
| 20 | 7.4 |
| 24 | 10.0 |

Figure 6:
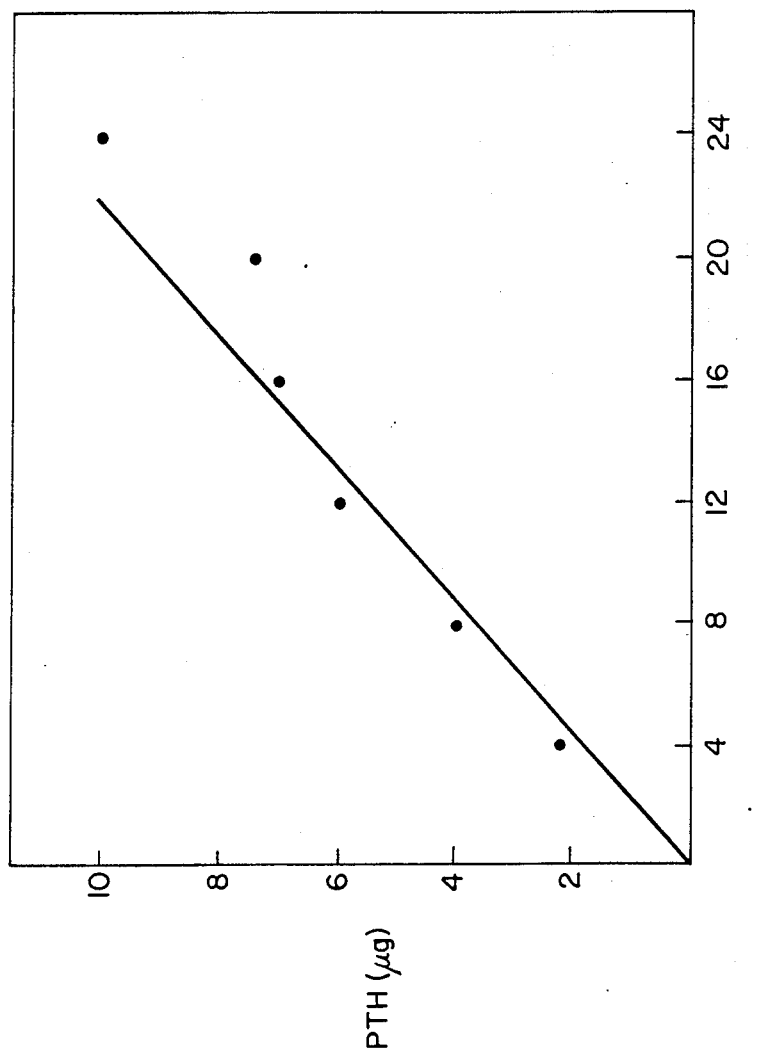
FIG. 6 is a graph prepared according to Example 4 representing the quantity of parathyroid hormone secreted in the designated time periods.

B. Calculation of PTH secretion rate and estimation of size of graft necessary for effective PTH delivery The rate of PTH secretion by the keratinocytes was determined from the slope of the plot of quantity of PTH secreted vs. time (FIG. 6). Use of this information in conjunction with information on the surface area of the epithlium secreting PTH made it possible to calculate the rate of PTH production per square centimeter ($cm^2$) of epithelium. The rate of PTH production was determined in this manner to be 1.4 ng/4 minutes/$cm^2$. This was determined as follows: The rate of secretion is 425 ng/ml., as read from the slope of the curve shown in FIG. 6. The epithelium in the 75 $cm^2$ flask is equivalent to 20 $cm^2$ because, after it is detached from the flask with dispace, the epithelium shrinks to about one-fourth its size. Therefore, the rate per surface area is:

425 ng/hour/20 $cm^2$
7 ng/minute/20 $cm^2$
0.35 ng/minute/$cm^2$
1.4 ng/4 minutes/$cm^2$ From this information, the size of a graft necessary to deliver PTH at physiologically significant levels was determined. For example, PTH is present in plasma at a concentration of 1-5 pg/ml. and a 70 Kg man has 2730 ml. of plasma and a total PTH content of 13.6 ng. The half life of PTH in plasma is approximately 4 minutes. To supply 13.6 ng of PTH every 4 minutes (which is more than sufficient to meet the needs of a 70Kg man) a graft 9.7 $cm^2$ in size would be needed. A graft of this size would not only provide physiologically significant levels of PTH, but also be cosmetically acceptable to a patient (user) and convenient to graft. In addition, genetic modification of keratinocytes necessary to produce a graft of this size would be a reasonably easy task.

Industrial Utility

This invention has industrial applicability in providing hormones, enzymes and drugs to mammals, including humans, in need of such substances. For example, it can be used to provide a continuous supply of a hormone which otherwise would be administered on a periodic basis by injection or oral administration. It is particularly valuable in providing such substances, such as human growth hormone, which are needed for extended periods of time.

Equivalents

Those skilled in the art will recognize or be able to ascertain, using no more than routine experimentation, many equivalents to the specific materials and components described herein. Such equivalents are intended to be encompassed in the scope of the following claims.

We claim:

1. An in vivo delivery vehicle consisting essentially of transplantable epithelial cells expressing foreign genetic material which is DNA which does not occur in epithelial cells; DNA which occurs in epithelial cells but is not expressed in them at levels which are biologically significant; DNA which occurs in epithelial cells and has been modified so that it is expressed in epithelial cells; and any DNA which can be modified to be expressed by epithelial cells, alone or in any combination thereof.

2. An in vivo delivery vehicle of claim 1, in which the foreign genetic material additionally comprises genetic material encoding at least one selectable marker.

3. An in vivo delivery vehicle of claim 2 in which at least one selectable marker is a dominant selectable marker.

4. An in vivo delivery vehicle of claim 3 in which the dominant selectable marker is a gene encoding antibiotic resistance.

5. An in vivo delivery vehicle consisting essentially of transplantable keratinocytes expressing foreign genetic material which is DNA which does not occur in keratinocytes; DNA which occurs in keratinocytes but is not expressed in them at levels which are biologically significant; DNA which occurs in keratinocytes and has been modified so that it is expressed in keratinocytes; and any DNA which can be modified to be expressed by keratinocytes, alone or in any combination thereof.

6. An in vivo delivery vehicle of claim 5, in which the foreign genetic material additionally comprises genetic material encoding at least one selectable marker.

7. An in vivo delivery vehicle of claim 6, in which at least one selectable marker is a dominant selectable marker.

8. An in vivo vehicle of claim 7 in which the dominant selectable marker is a gene encoding antibiotic resistance.

9. An in vivo delivery vehicle consisting essentially of transplantable human keratinocytes expressing genetic material which is not normally expressed by human keratinocytes at biologically significant levels, and is genetic material incorporated into the keratinocytes in a retroviral vector.

10. An in vivo delivery vehicle of claim 9 in which the genetic material expressed encodes a hormone, an enzyme, a receptor or a drug.

11. An in vivo delivery vehicle of claim 10, additionally comprising genetic material which encodes at least one dominant selectable marker.

12. An in vivo delivery vehicle consisting essentially of transplantable keratinocytes expressing genetic material present in the keratinocytes in a retroviral vector, the genetic material selected from the group consisting of: DNA which does not occur in keratinocytes; DNA which occurs in keratinocytes but is not expressed in them at levels which are biologically significant; DNA which occurs in keratinocytes and has been modified so that it is expressed in keratinocytes; and DNA which can be modified to be expressed by keratinocytes.

13. An in vivo delivery vehicle consisting essentially of transplantable keratinocytes having incorporated therein recombinant amphotropic retrovirus having a recombinant genome comprised of:
   a. long terminal repeat sequences, the tRNA binding site and the Psi packing site derived from amphotropic Moloney murine leukemia virus;
   b. genetic material encoding at least one selectable marker; and
   c. genetic material encoding a selected protein of mammalian origin or a selected polypeptide of mammalian origin.

14. An in vivo delivery vehicle of claim 13 in which the genetic material encoding at least one dominant selectable marker is a neo gene.

15. An in vivo delivery vehicle of claim 13 in which the genetic material encodes human growth hormone.

16. The keratinocytes of ATCC CRL8858 in culture.

* * * * *